(12) United States Patent
Roychowdhury

(10) Patent No.: US 7,138,046 B2
(45) Date of Patent: *Nov. 21, 2006

(54) PROCESS FOR PRODUCTION OF HYDROGEN FROM ANAEROBICALLY DECOMPOSED ORGANIC MATERIALS

(75) Inventor: Sukomal Roychowdhury, San Diego, CA (US)

(73) Assignee: World Hydrogen Energy LLC, Maspeth, NY (US)

( * ) Notice: Subject to any disclaimer, the term of this patent is extended or adjusted under 35 U.S.C. 154(b) by 492 days.

This patent is subject to a terminal disclaimer.

(21) Appl. No.: 09/932,014

(22) Filed: Aug. 17, 2001

(65) Prior Publication Data

US 2003/0205458 A1    Nov. 6, 2003

Related U.S. Application Data

(60) Division of application No. 09/472,274, filed on Dec. 27, 1999, now abandoned, which is a continuation-in-part of application No. 08/659,644, filed on Jun. 6, 1996, now Pat. No. 6,090,266.

(51) Int. Cl.
*C25B 1/00* (2006.01)

(52) U.S. Cl. .................. 205/637; 205/688; 205/698

(58) Field of Classification Search ............... 205/637, 205/688, 698; 322/2 R
See application file for complete search history.

(56) References Cited

U.S. PATENT DOCUMENTS 4,053,395 A    10/1977  Switzgable
4,124,481 A    11/1978  Ramer
4,200,505 A *  4/1980   Day et al. .................. 205/343
4,341,608 A *  7/1982   St. John ..................... 205/639
4,389,288 A    6/1983   Vaughan
4,395,316 A    7/1983   St. John
5,254,934 A *  10/1993  Carabetta et al. .......... 322/2 R
6,090,266 A *  7/2000   Roychowdhury .......... 205/637

FOREIGN PATENT DOCUMENTS

| DE | 244742 A | * | 4/1987 |
| GB | 2 076 849 A | | 12/1981 |
| GB | 2 149 423 A | | 6/1985 |
| GB | 2 190 682 A | | 11/1987 |
| JP | 07 031998 | | 2/1995 |
| WO | WO 94/08907 | * | 4/1994 |

* cited by examiner

*Primary Examiner*—Arun S. Phasge
(74) *Attorney, Agent, or Firm*—Kramer Levin Naftalis & Frankel LLP; Barry Evans, Esq.

(57) ABSTRACT

A process for the production of hydrogen from anaerobically decomposed organic materials by applying an electric potential to the anaerobically decomposed organic materials, including landfill materials and sewage, to form hydrogen, and for decreasing the time required to treat these anaerobically decomposed organic materials. The organic materials decompose to volatile acids such as acetic acid, which may be hydrolyzed by electric current to form hydrogen. The process may be continuously run in sewage digestion tanks with the continuous feed of sewage, at landfill sites, or at any site having a supply of anaerobically decomposed or decomposable organic materials.

14 Claims, 8 Drawing Sheets

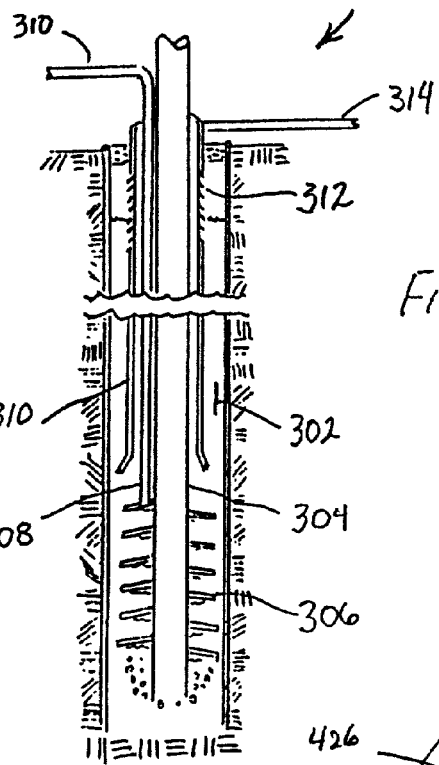
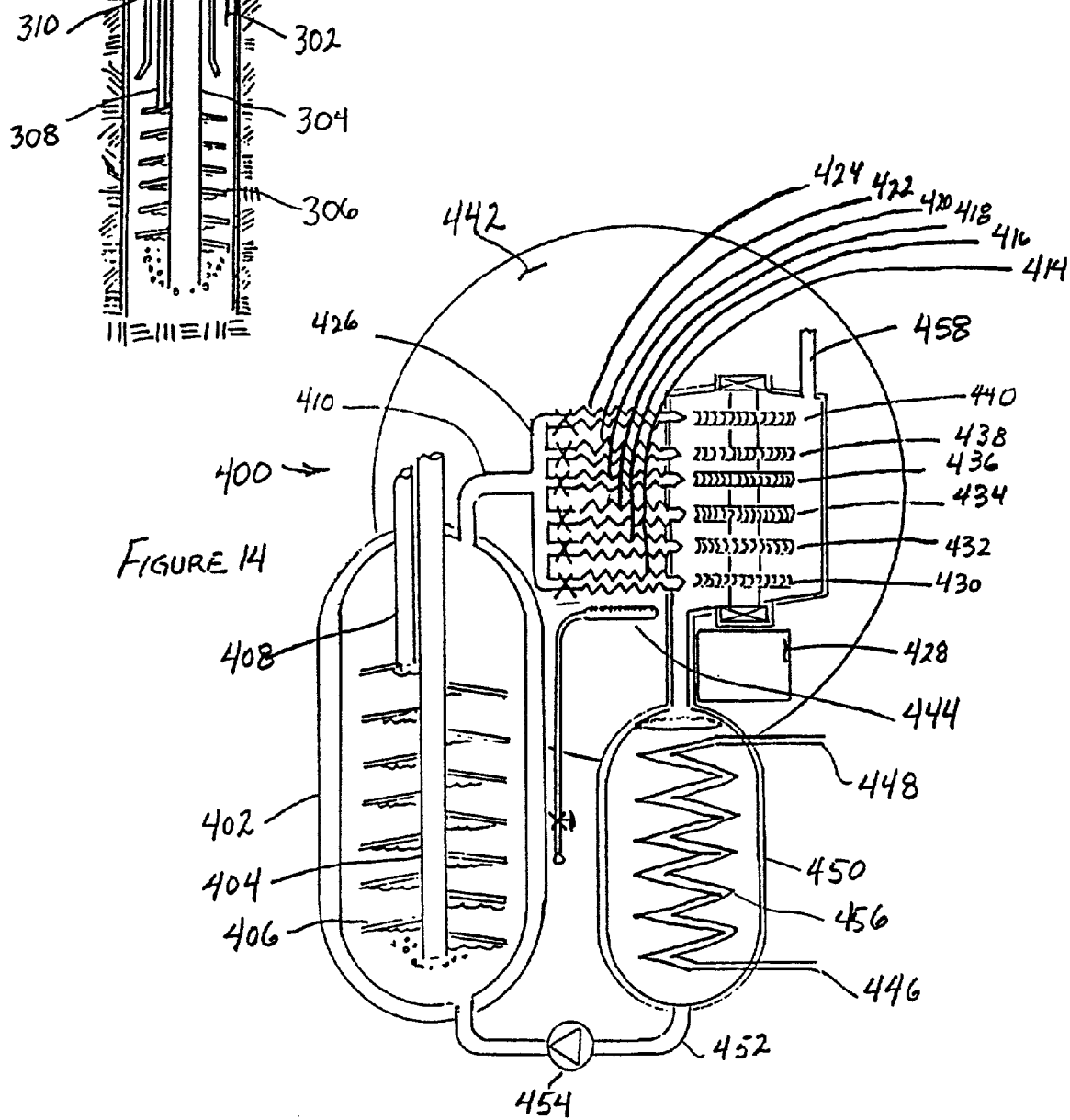

PROCESS FOR PRODUCTION OF HYDROGEN FROM ANAEROBICALLY DECOMPOSED ORGANIC MATERIALS

CROSS-REFERENCE TO RELATED APPLICATION

This application is a divisional of U.S. application Ser. No. 09/472,274, filed Dec. 27, 1999, now abandoned which is a continuation-in-part of U.S. application Ser. No. 08/659,644, filed Jun. 6, 1996, now U.S. Pat. No. 6,090,266, all of which are incorporated herein by reference.

BACKGROUND OF THE INVENTION

It is recognized that additional sources of energy are needed for sustained industrial growth. There exists an ever present danger in depending too heavily on fossil fuels. Fossil fuels (hydrocarbons) represent a limited supply of stored energy which are typically released during a combustion process. By burning hydrocarbons mankind has spewed billions of tons of toxic pollutants into the atmosphere. It therefore makes sense from both an environmental and economic standpoint to develop alternative sources of renewable fuels.

Hydrogen is a fuel which does not produce pollutants, water being its only combustion product. Hydrogen has many industrial uses in the production of fertilizers, dyes, drugs, plastics, hydrogenated oils and fats and methanol and is used in many industries. It is also used as a rocket fuel and in this invention as a minus-emissions fuel that allows ordinary engines to clean the air.

1. Field of the Invention

This invention relates to a process for the production of hydrogen from anaerobically decomposed organic materials, including materials such as those found in landfill materials and sewage sludge, by applying an electric potential to and thereby creating a current through the anaerobically decomposed organic material and thereby forming hydrogen.

2. Description of Related Art

The established processes for producing commercially significant amounts of hydrogen are: (1) steam reforming of hydrocarbons, (2) partial oxidation of coal, (3) electrolysis of water, and (4) direct use of solar radiation (photovoltaic method).

Steam-reformation of hydrocarbons and partial oxidation of coal are disadvantageous in that fossil hydrocarbon fuels are consumed. Production of hydrogen by electrolysis of water, a relatively simple and non-polluting process, is costly and therefore economically disadvantageous for most industrial applications because the amount of energy needed for electrolysis of water exceeds the energy obtained from the combustion of the resulting hydrogen. Photovoltaic methods of hydrogen production have inherent inadequacy related to access to solar radiation for much of the world's population.

Unlike the methods for production of hydrogen outlined above, the process of the present invention does not depend on fossil fuels or the somewhat random appearance of sunlight to produce hydrogen. The present process converts what are typically waste materials into hydrogen, while simultaneously reducing the mass of said materials and/or reducing the treatment time of such materials by application of a relatively small and/or intermittent electric potential to said materials. The process of this invention uses raw materials typically found in, among other places, municipal waste sites and sewage treatment plants and produces more energy, in the form of the chemically stored potential energy of hydrogen, than the electric energy required to produce the hydrogen.

A method of producing hydrogen from sugars is discussed in *Energy and the Environment*, Proceedings of the 1st World Renewable Energy Congress, Reading, UK Sep. 23–28, 1990. S. Roychowdhury and D. Cox ("Roychowdhury"). This method involves the production of hydrogen from pure sugars such as glucose or maltose.

Roychowdhury reports the initial production of hydrogen upon inoculation of a sugar solution with so-called "landfill inocula". To obtain landfill inocula, materials were obtained from various depths in a landfill, dried, ground (to obtain "landfill powder") and then incubated in situ. The incubated culture medium was observed to produce carbon dioxide and methane, primarily, and little else, indicating the presence of highly methanogenic flora in the inoculum. The supernatant from this culture medium, or in some cases the landfill powder, were used as inocula.

Previously, Roychowdhury disclosed that upon inoculation of various sugar solutions with the landfill supernatant or landfill powder, the sugar solution produced hydrogen and carbon dioxide, and no methane or oxygen; indicating the presence of hydrogen-producing bacteria present in the landfill inoculum and/or landfill hydrogen. Hydrogen production decreased with increasing acidity.

It is another object of this invention to provide a method of hydrogen production which does not require the use of fossil fuels.

It is an object of the invention to serve communities that have relatively undeveloped electricity distribution and other energy infrastructures with a system that provides useful energy from collected wastes.

It is an object of the present invention to separate carbon dioxide, nitrogen and other gases from produced hydrogen.

SUMMARY OF THE INVENTION

This invention relates generally to a process which produces hydrogen from anaerobically decomposed organic materials such as anaerobically composted cellulosic materials and anaerobically digested sewage sludge. This process decreases the time required to treat anaerobically composed cellulosic materials and anaerobically digested sewage sludge. More specifically, the invention relates to an embodiment wherein a relatively low electric potential is applied to anaerobically decomposed organic materials such as anaerobically composted cellulosic waste materials and anaerobically digested sewage sludge which, as a result of anaerobic decomposition, have been fermented into "volatile" carboxylic acids such as acetic acid and bicarbonates of ammonia. The electric current resulting from the application of an electric potential is believed to hydrolyze the acetic acids, other volatile carboxylic acids, and bicarbonates of ammonia within the decomposed materials, thereby producing hydrogen. Formation of methane is suppressed, Organic mass, such as solids contained within sewage sludge is reduced at an increased rate, and the time required to treat waste materials such as sewage sludge is thereby reduced.

In another embodiment the time of application of electropotential is intermittent and the duty cycle of voltage application is adaptively adjusted to minimize electric power consumption while maximizing hydrogen production. In application it is believed that the activities of microorganisms that produce enzymes that release hydrogen from the ferment is greatly encouraged and that activities of microorganisms that produce enzymes favoring methane production are depressed.

BRIEF DESCRIPTION OF THE DRAWINGS

FIG. 13 is a schematic illustrating the principles of another embodiment of the invention.

FIG. 14 is a schematic illustrating the principles of another embodiment of the invention.

DETAILED DESCRIPTION OF THE INVENTION

Figure 1:
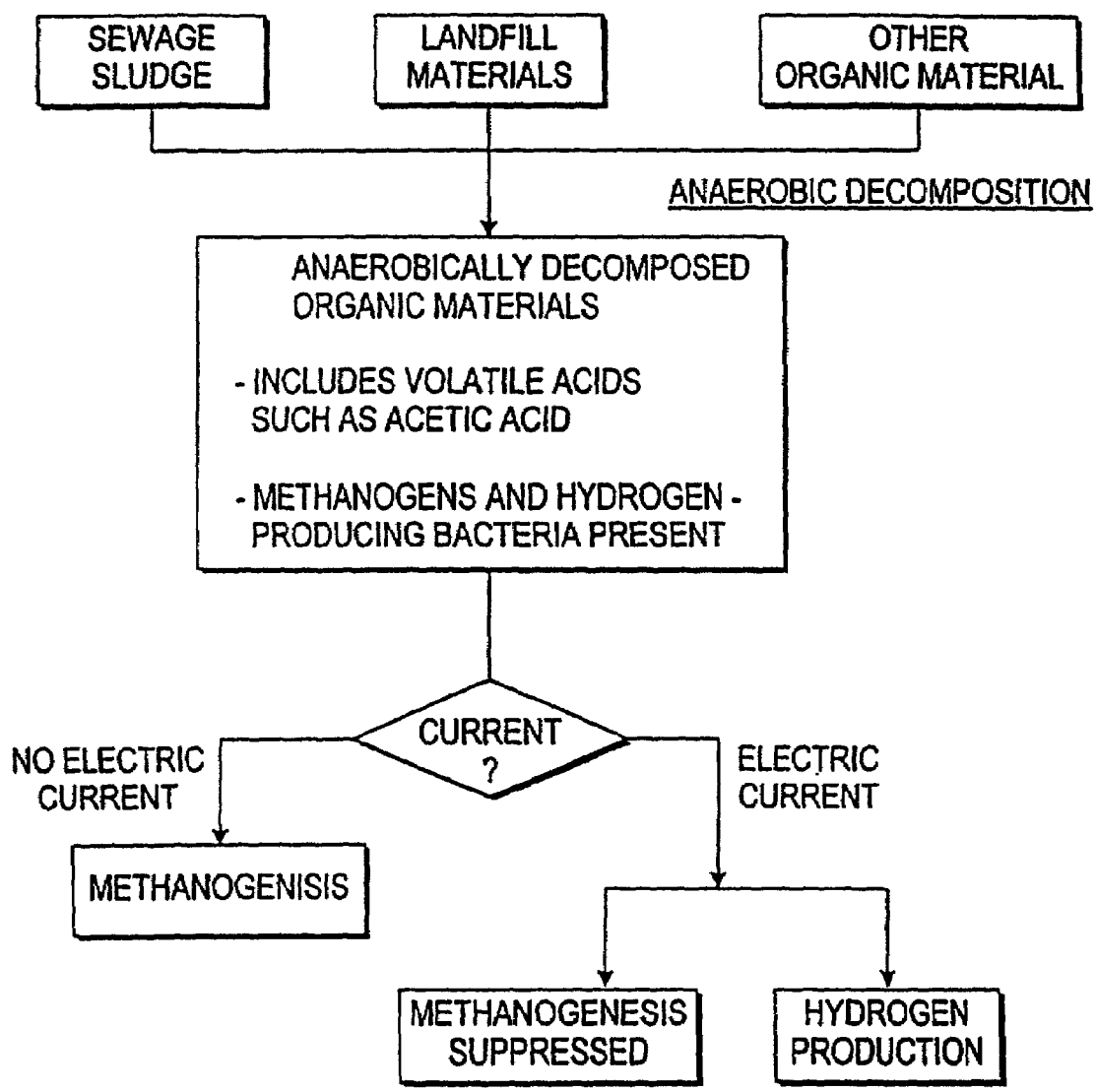
FIG. 1 is a flow chart showing both production of hydrogen and suppression of methaneogenesis from anaerobically decomposed organic materials in the presence of an applied electropotential, and methanogenesis from anaerobically decomposed organic materials in the absence of an applied electropotential.
Figure 2:
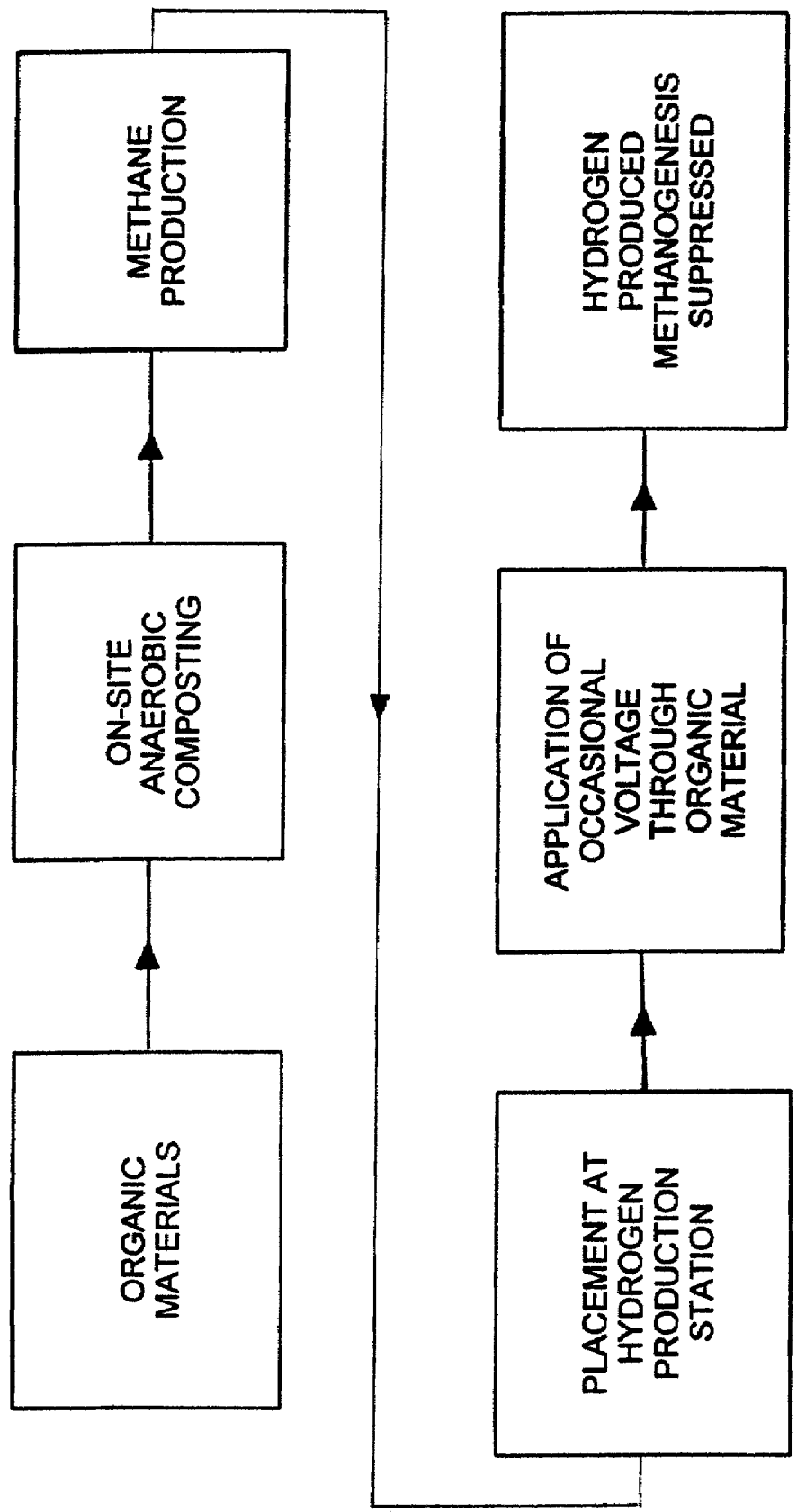
FIG. 2 is a flow chart showing a process for production of hydrogen which includes on-site anaerobic decomposition of organic material.

The process of the present invention may typically be practiced at any large municipal landfill or sewage treatment facility, but can be practiced on a smaller scale wherever anaerobically decomposed organics such as anaerobically composted cellulosic materials or anaerobically digested sewage sludge are found or may be generated.

Anaerobically composted cellulosic materials are typically found in landfill materials. Anaerobically digested sewage sludge typically comprises sludge found at municipal sewage treatment plants. Landfill materials generally consist of approximately 70% cellulosic materials and have a moisture content of 36% to 46%. Sewage sludge is primarily liquid, contains volatile acids such as acetic acid, and includes 2–3% solids. Both landfill materials and sewage sludge naturally contain methane-producing abacterial species and hydrogen-producing bacterial species.

The invention may be practiced by applying an electric potential of between 1 and 7 volts, preferably between 3 and 6 volts, most preferably between 3.0 and 4.5 volts to, and thereby passing an electric current through, anaerobically decomposed organic materials such as landfill materials or sewage sludge. This electric potential is applied through electrodes which are preferably made from lead, copper, steel, brass or carbon, more preferably from cast iron bars, and most preferable from metal impregnated or otherwise electrically conductive graphite.

Anaerobic decomposition, specifically anaerobic composting and anaerobic digestion, refers to a process where organic compounds, typically but not limited to compounds of the general formula $C_nH_{2n}O_n$, decompose in the absence of an oxygen-donor environment. Volatile acids such as acetic acid are typically formed by such anaerobic decomposition. Although anaerobic decomposition may in some instances be preceded by aerobic decomposition, aerobic decomposition is not a prerequisite to anaerobic decomposition and electrodes can be placed within the organic materials prior to the commencement of anaerobic decomposition.

As described above, both landfill materials comprising anaerobically composted cellulosic materials and anaerobically digested sewage sludge contain relatively high amounts of volatile acids such as acetic acid. These acids are known to act as electrolytes. In practicing the invention, one or more sets of electrodes may be placed within landfill material or sewage sludge in such a way that an electric potential is applied, and according to the principles of the invention resulting in an electrical current with low polarization and ohmic losses. Electrode distance and placement along with the program of voltage control including occasional reversal of polarity may be adjusted to achieve these conditions. The voltage, average spacing of electrodes and number of electrodes will vary depending upon the size and composition of the landfill material or sewage sludge sought to be used to produce hydrogen. Electrode sets, may be of any suitable shape, e.g. plates, bars, grids, etc.

In a preferred embodiment of the invention, each individual electrode is placed into landfill materials and is surrounded by an inert "cage" which effectively ensures that the moisture component of the landfill materials, and not a component which might interfere with electrical activity, is immediately adjacent each electrode. Place of the electrodes in a suitable position within the landfill material may require some trial and error.

When an electric potential is applied, hydrogen production begins and production of hydrogen increases to from 70% to 75% by volume of the total gases produced. The level of methane produced decreases from a high of approximately 70% by volume of the total gases produced, when the electric current is first applied, to greatly diminished trace levels. Carbon dioxide and nitrogen production remain relatively constant and do not vary significantly with methane or hydrogen production.

Without being bound by theory, it is believed that the essence of the electrochemistry of this invention is the enzyme facilitated production and decomposition of low molecular weight volatile acids such as acetic acid produced by bacterial breakdown of carbohydrates and other nutrients. Because oxygen production is not observed, it is believed that electrolysis of water is not a source of hydrogen. It is further believed that hydrogen gas produced by the electrolysis of volatiles present in the sludge and in landfill materials, inhibits the subdivision, growth, and activity of methanogenic species.

In a preferred embodiment, cellulosic materials and/or sewage sludge are made to decompose "on-site", i.e. in a localized bin or chamber, rather than at a centralized landfill or sewage treatment facility. The anaerobically composted cellulosic waste materials and/or the anaerobically digested sewage sludge are then optionally taken to a transfer station equipped with electrodes as previously described to produce hydrogen, or alternatively made to produce hydrogen "on-site" by application of electric potential at or near the on-site bin or chamber. In this alternate embodiment, hydrogen could then be stored or used on-sites as a energy source to produce useful forms of energy including the relatively minor amount used to practice the principles of the invention.

EXAMPLES: ELECTRODES

Electrodes were cast iron bars, 300 mm long, 25 mm wide and 2.5 mm thick. Other metallic electrodes were used including lead, copper, steel, brass and others. pair of copper impregnated graphite electrodes of the same size was used. Degradation of the graphite electrode was not very noticeable.

Landfill Materials

Samples of landfill material were obtained from a sanitary landfill at Staten Island N.Y. from a depth of between 30 to 50 feet. The landfill materials naturally produce methane and carbon dioxide as primary gases (in 55:35 proportions) through methanogenesis.

Sludge

Sludge samples were taken from a primary digester of a sewage treatment plant at Brooklyn, N.Y. Sewage sludge produces methane and carbon dioxide (in 65:30 proportions) by methanogenesis.

Special Apparatus

A series of experiments were set up to determine whether the production of hydrogen would take place when voltage was applied through either sewage sludge or through landfill materials. The pH of the sludge was 7.0–7.5 and the pH of the landfill material was 6.5–7.0. Apparatus included on 800 ml flask with a three hole rubber stopper. Two of those holes were fitted with electrodes and the third hole had a glass delivery tube. The electrodes and the third hole had a glass delivery tube. The electrodes were connected across two 1.5 volt batteries in series, resulting in an applied potential of about 3.0 volts. The apparatus was placed in an incubator set either at 37° C. and later at 55° C. Other apparatus included a New Brunswick Fermenter using a 6–8 liter glass vessel where the temperature, and rotating stirrer and a cooling system could be controlled at a desired setting.

Experimental Data

Example 1

Figure 3:
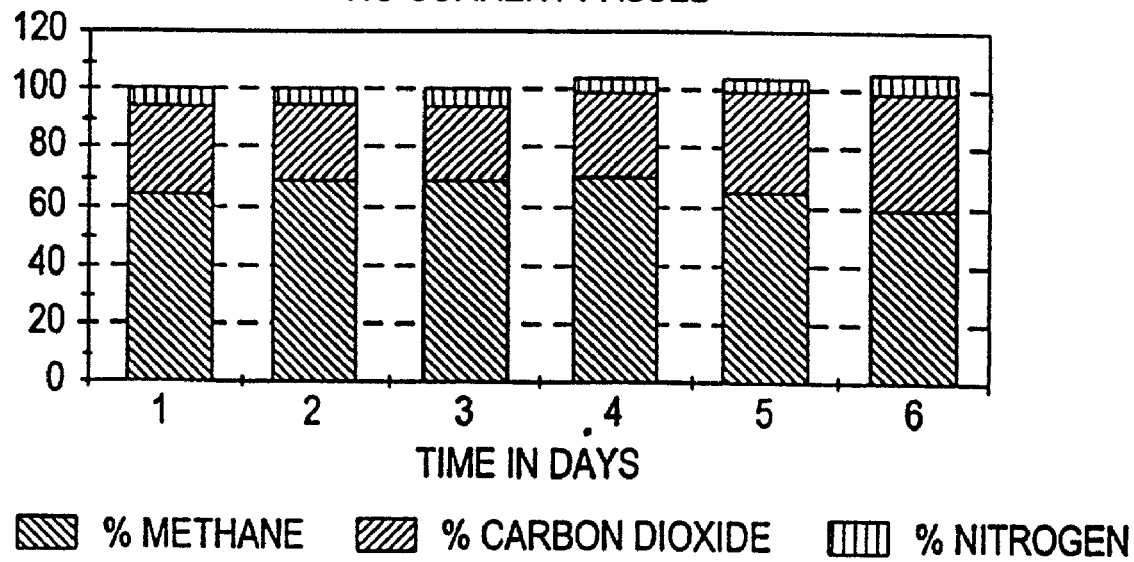
FIG. 3 is a bar graph representation of the information in Table 1.

As an experimental control, freshly obtained sewage sludge in an 800 ml flask was placed at 37° C. in an incubator gases, including primarily methane, were produced as described at Table 1 and depicted at FIG. 3.

TABLE 1

Production of $CH_4$ and $CO_2$

| DAYS | % $CH_4$ | % $CO_2$ | % $N_2$ |
|---|---|---|---|
| 1 | 65 | 30 | 5 |
| 2 | 70 | 25 | 5 |
| 3 | 70 | 25 | 5 |
| 4 | 65 | 30 | 4 |
| 5 | 60 | 35 | 4 |
| 6 | 55 | 40 | 5 |

Example 2

Figure 4:
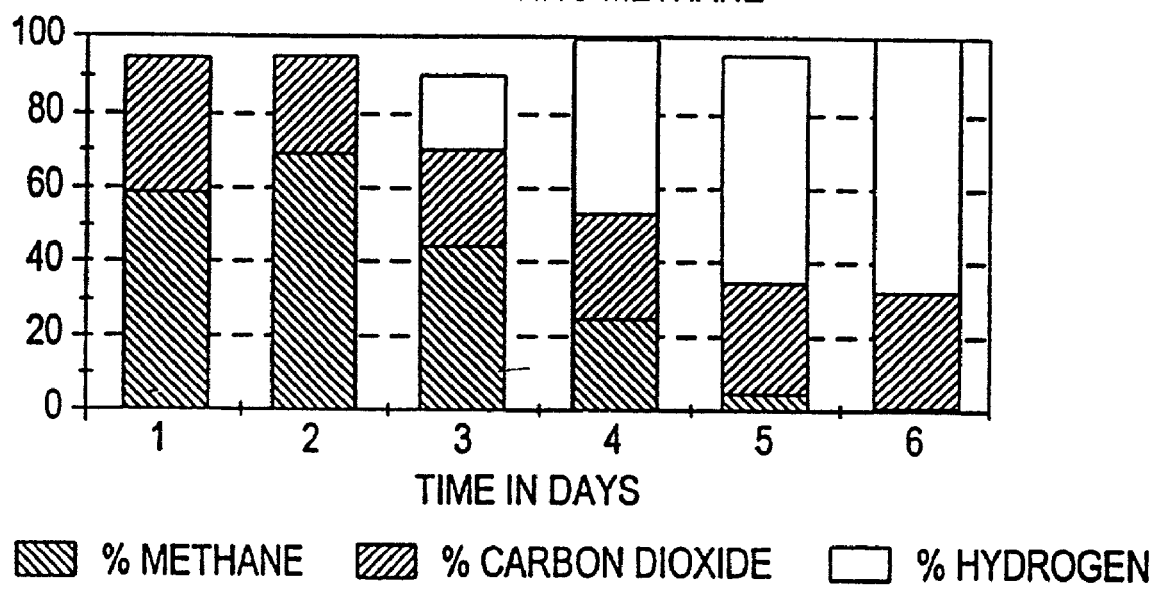
FIG. 4 is a bar graph representation of the information in Table 3.

Sewage sludge from the primary digester was placed in an 800 ml flask which was then placed in a preheated incubator at 37° C. Methane gas was generated. As soon as optimum production of methane was achieved, a current was passed through the liquid in the flask. The production of methane gas declined gradually and hydrogen and carbon dioxide were produced. Methane was completely suppressed when production of hydrogen reached its peak, as described at Table 2 and depicted at FIG. 4.

TABLE 2

Production of $H_2$ and Suppression of $CH_4$

| DAYS | % $CH_4$ | % $CO_2$ | % $H_2$ |
|---|---|---|---|
| 1 | 60 | 35 | — |
| 2 | 70 | 25 | — |
| 3* | 45 | 25 | 20 |
| 4 | 25 | 28 | 46 |
| 5 | 5 | 30 | 60 |
| 6 | TR | 30 | 68 |

Example 3

Figure 5:
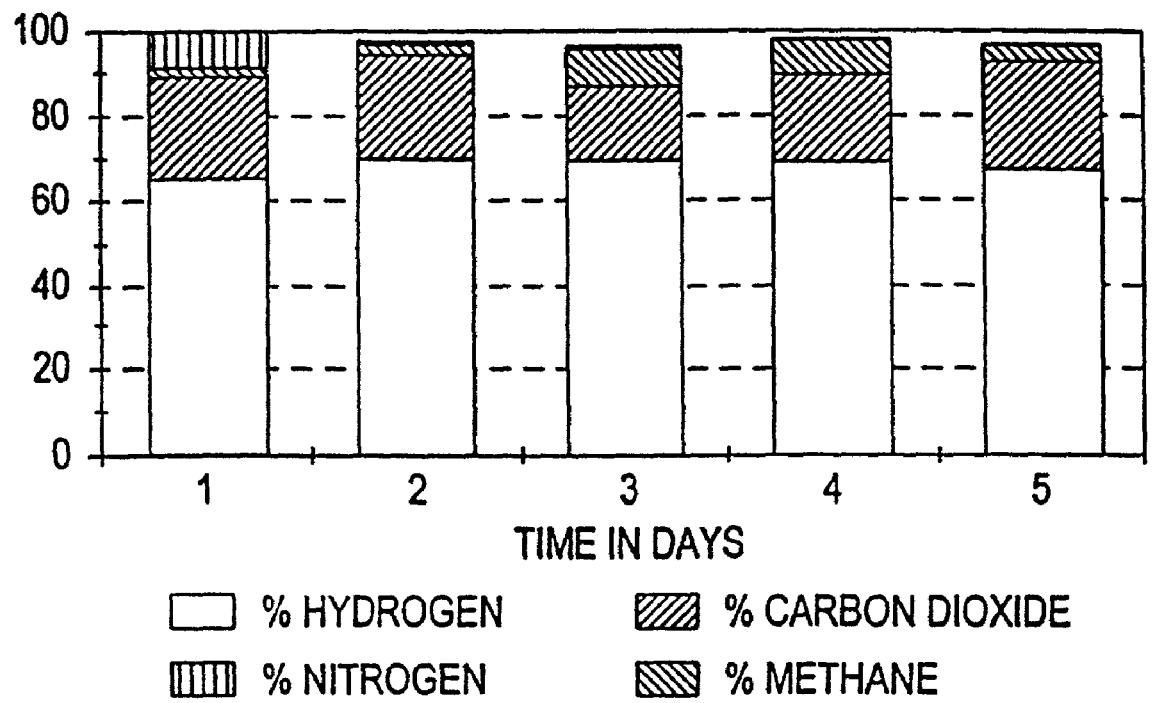
FIG. 5 is a bar graph representation of the information in Table 3.

Sewage sludge from the primary digester was placed in an 800 ml flask which was then placed in an incubator at 37° C. A current was passed through the sludge, applying 3 volts, using the two 1.5 volt batteries in series. Very little methane was produced at the beginning. Within 3 days, production of hydrogen reached its peak and methane gas was virtually totally suppressed, as described at Table 3 and depicted at FIG. 5.

TABLE 3

Production of $H_2$ and $CO_2$ When Voltage Was Applied From the Start

| DAYS | % $H_2$ | % $CO_2$ | % $N_2$ | % $CH_4$ |
|---|---|---|---|---|
| 1 | 65 | 25 | 2 | 8 |
| 2 | 70 | 25 | 2 | TR |
| 3 | 70 | 18 | 8 | TR |
| 4 | 70 | 20 | 8 | — |
| 5 | 68 | 25 | 4 | — |

Example 4

A sewage sludge sample was placed in a five liter flask in the New Brunswick Fermenter and 4 electrodes were introduced. Electrical current was passed through (2.5 volts and 0.05 to 0.07 Amps). In the beginning only methane and carbon dioxide were produced with very little hydrogen. As soon as the voltage was increased to 4.0–4.5, and current to 0.11–0.15 Amps, methane was gradually suppressed and hydrogen was produced as described at Table 4.

TABLE 4

Production of $H_2$ and $CO_2$, From Sludge in 5 liter Container

| DAYS | % $H_2$ | % $CO_2$ | % $N_2$ | % $CH_4$ |
|---|---|---|---|---|
| 1 | — | 30 | 12 | 50 |
| 2 | 5 | 35 | 8 | 46 |

TABLE 4-continued

Production of $H_2$ and $CO_2$, From
Sludge in 5 liter Container

| DAYS | % $H_2$ | % $CO_2$ | % $N_2$ | % $CH_4$ |
|---|---|---|---|---|
| 3 | 4 | 30 | 6 | 60 |
| 5 | 25 | 30 | 5 | 40 |
| 6 | 48 | 25 | 5 | 20 |
| 7 | 60 | 20 | 2 | 8 |
| 9 | 70 | 25 | 4 | TR |

Example 5

It is of particular interest to treat landfill materials because these materials present municipalities around the world with ubiquitous problems of vector (rodents, roaches, and communicable disease germs) breeding places along with sources of greenhouse gases and groundwater contamination due to production of poisonous leachate. The present invention provides for carbon sequestration from landfills including those that are depositories for sewage sludge.

Figure 6:
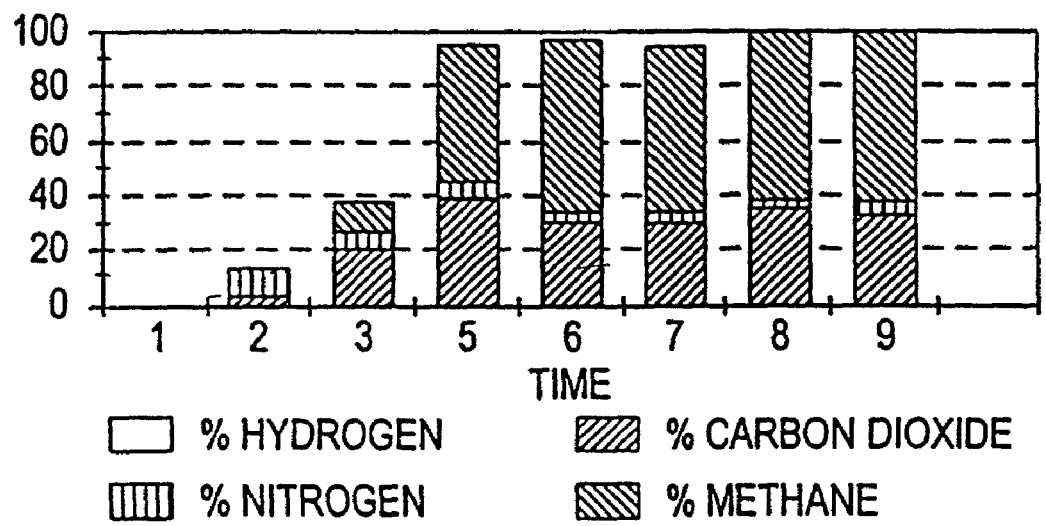
FIG. 6 is a bar graph representation of the information in Table 5.
Figure 7:
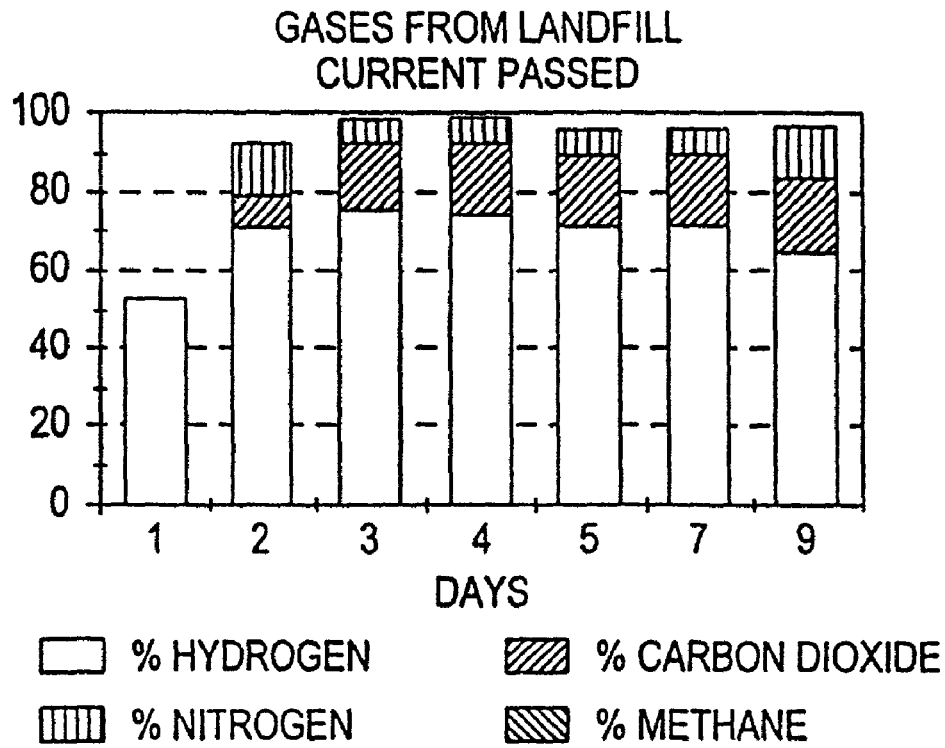
FIG. 7 is a bar graph representation of the information in Table 6.

Landfill materials collected by random borings were provided for determination of the least energy expenditures per energy production. Experiments were set up with landfill materials (composted municipal solid wastes) in two 800 ml flasks, (1) with landfill materials only, (2) with landfill materials where electrodes were dipped in. The results are described at Tables 5 and 6, and depicted at FIGS. 6 and 7.

TABLE 5

Production of Gases From Landfill Materials

| DAYS | % $H_2$ | % $CO_2$ | % $N_2$ | % $CH_4$ |
|---|---|---|---|---|
| 1 | — | — | — | — |
| 2 | — | 3 | 10 | — |
| 3 | — | 20 | 8 | 10 |
| 5 | — | 40 | 6 | 50 |
| 6 | — | 30 | 5 | 63 |
| 7 | — | 30 | 5 | 60 |
| 8 | — | 35 | 4 | 60 |
| 9 | — | 35 | 5 | 62 |

TABLE 6

Production of Gases From Landfill
Materials in Presence of Applied Voltage

| DAYS | % $H_2$ | % $CO_2$ | % $N_2$ | % $CH_4$ | Total CC |
|---|---|---|---|---|---|
| 1 | 53 | — | All | — | 95 |
| 2 | 72 | 8 | 13 | — | 302 |
| 3 | 76 | 17 | 6 | — | 500 |
| 4 | 75 | 18 | 6 | — | 600 |
| 5 | 72 | 18 | 6 | — | 450 |
| 7 | 79 | 18 | 6 | — | 600 |
| 9 | 65 | 18 | 14 | — | 500 |

Example 6

Figure 8:
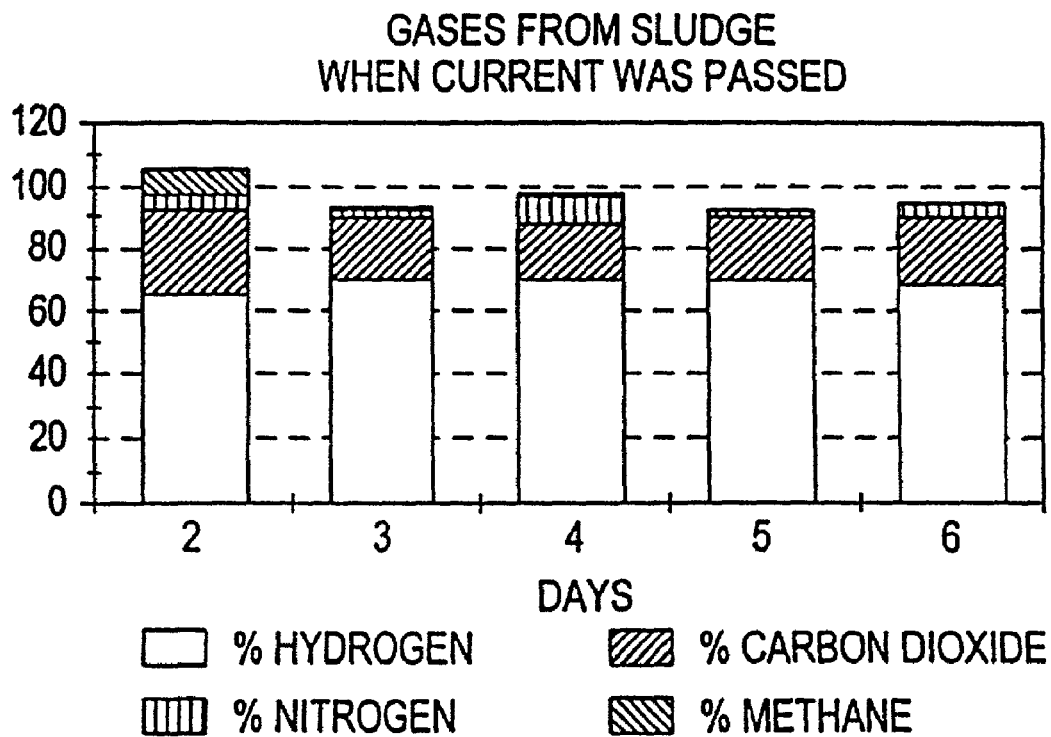
FIG. 8 is a bar graph representation of the information in Table 8.

Example 5 was repeated: (1) with sludge only, (2) with sludge having operating electrodes. The results are described at Tables 7 and 8, and depicted FIG. 8.

TABLE 7

Production of Gases From Sludge
in Absence of Applied Voltage

| DAYS | % $H_2$ | % $CO_2$ | % $N_2$ | % $CH_4$ | Total CC |
|---|---|---|---|---|---|
| 2 | — | 20 | 14 | 65 | 50 |
| 3 | — | 14 | 10 | 70 | 125 |
| 4 | — | 19 | 4 | 72 | 225 |
| 5 | — | 22 | 4 | 66 | 258 |
| 6 | — | 18 | 8 | 70 | 200 |

TABLE 8

Production of Gases From Sludge
in Presence of Applied Voltage

| DAYS | % $H_2$ | % $CO_2$ | % $N_2$ | % $CH_4$ | Total CC |
|---|---|---|---|---|---|
| 2 | 65 | 28 | 4 | 8 | 85 |
| 3 | 70 | 20 | 2 | TR | 200 |
| 4 | 70 | 18 | 8 | TR | 310 |
| 5 | 70 | 20 | 2 | — | 330 |
| 6 | 68 | 22 | 4 | — | 258 |

Example 7

Figure 9:
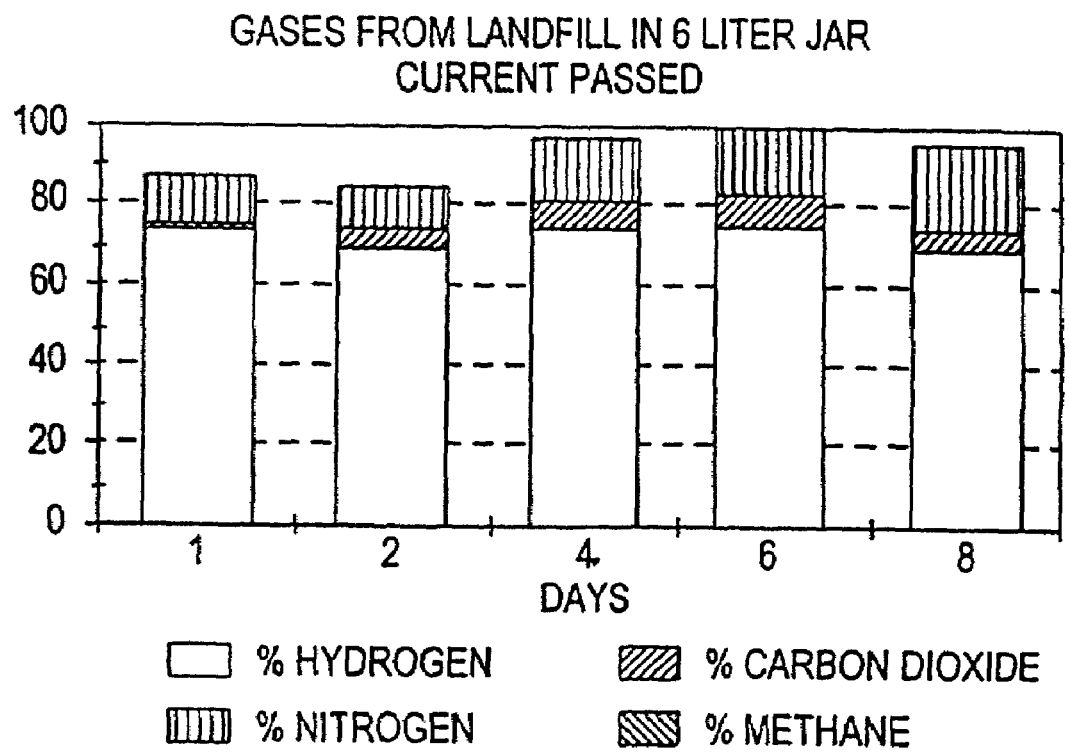
FIG. 9 is a bar graph representation of the information in Table 9.

An experiment was set up with landfill materials in a 6 liter vessel with electrodes. A current was created through the landfill materials by applying an electric potential of 3.5 V. The results are described at Table 9 and depicted at FIG. 9.

TABLE 9

Production of Gases From Landfill Materials
in 6 Liter Vessel With Applied Voltage

| DAYS | % $H_2$ | % $CO_2$ | % $N_2$ | % $CH_4$ | TOTAL |
|---|---|---|---|---|---|
| 1 | 75 | TR | 12 | — | 100 |
| 2 | 70 | 5 | 10 | — | 1020 |
| 4 | 75 | 7 | 15 | — | 850 |
| 6 | 75 | 8 | 17 | — | 750 |
| 8 | 70 | 5 | 20 | — | 600 |

Example 8

Figure 10:
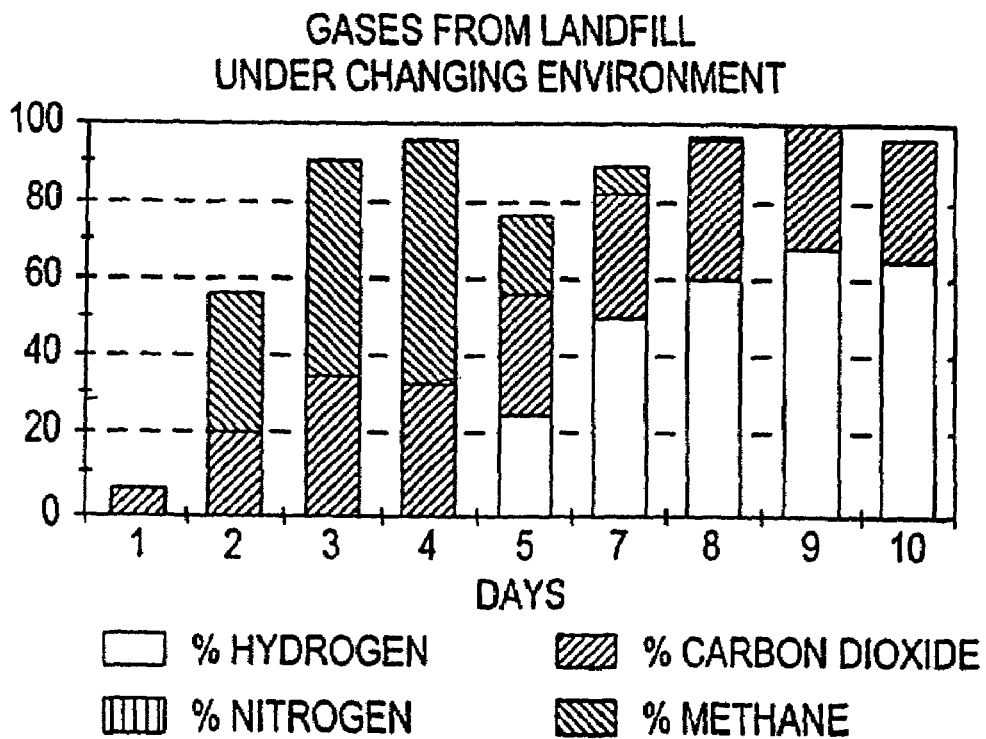
FIG. 10 is a bar graph representation of the information in Table 10.

Landfill materials in a 6 liter vessel were placed in a preheated incubator at 55° C. After 4 days electrodes were connected to 3.5 volt terminals. The results are described at Table 10, and depicted at FIG. 10.

Similar results are achieved by mixing a relatively small amount of inoculum of human sewage sludge with farm manure and/or crop wastes. After an incubation period in which anaerobic conditions were established, methane and carbon dioxide were produced with very little hydrogen. Upon presentation of voltage at 2.0 to 5.0 volts to cause current to reach 0.10 to 0.20 Amps, methane production was depressed and hydrogen was again produced as summarized in Table 10. Similar results are achieved by use of inoculum from previous runs of Example 4 and provide improvements in the efficiency of conversion of chemical energy potential of organic substances 25 into hydrogen.

TABLE 10

Production of Gas from landfill Materials
in Two Different Environments In the Same Set-Up

| DAYS | % $H_2$ | % $CO_2$ | % $N_2$ | % $CH_4$ | TOTAL |
|------|---------|----------|---------|----------|-------|
| 1    | —       | 5        | All     | —        | 20    |
| 2    | —       | 20       |         | 35       | 125   |
| 3    | —       | 35       |         | 55       | 200   |
| 4    |         |          |         |          |       |
| 5*   |         | 30       |         | 20       | 150   |
| 7    | 25      | 31       |         | 7        | 150   |
| 8    | 60      | 35       |         | TR       | 250   |
| 9    | 68      | 31       |         | —        | 285   |
| 10   | 65      | 30       |         | —        | 200   |

Figure 11:
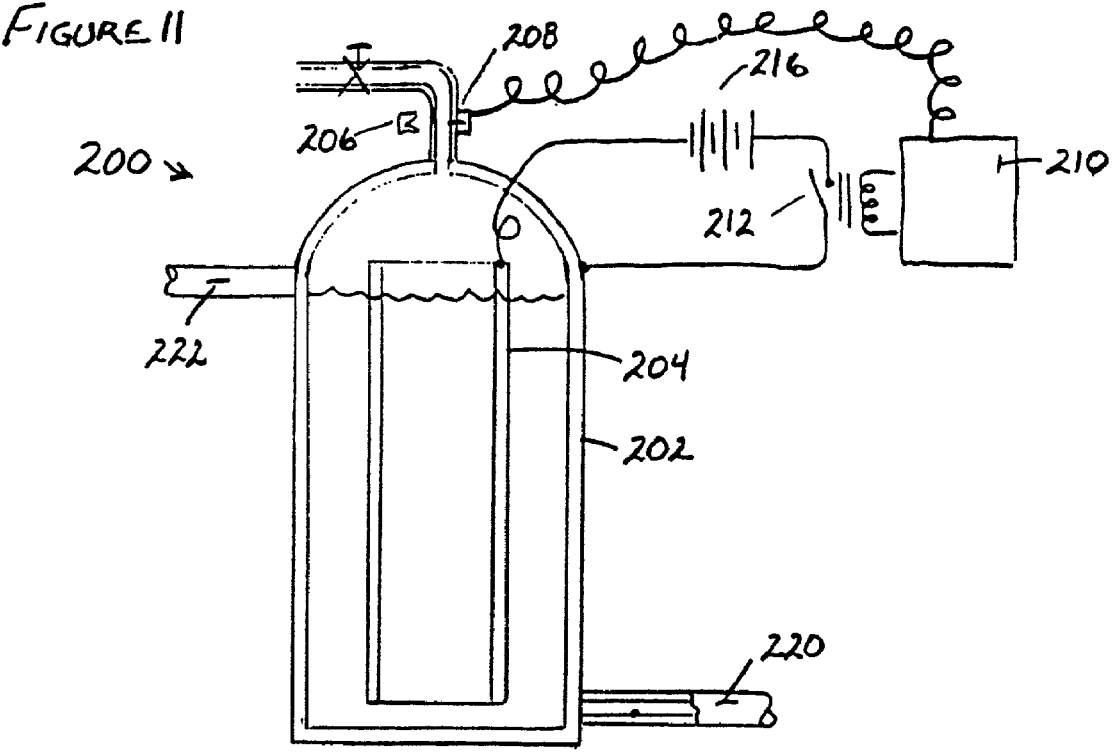
FIG. 11 is a schematic illustration of an embodiment that adaptively controls application of intermittently applied voltage to maximize hydrogen production while minimizing methane production.

FIG. 11 shows an embodiment 200 in which suitable electrodes such as concentric electrodes 202 and 204 receive intermittently applied voltage to influence the solvated organic waste between the electrodes to produce hydrogen more or less according to the data shown in Tables 8, 9, and 10. In operation, voltage is applied by voltage source 216 according to a duty cycle controlled by relay 212 that is constantly adjusted by controller 210 to facilitate hydrogen generation and to prevent substantial methane production.

Feedback information from gas detector 206/208 is provided to controller 210. If trace amounts of methane are detected a voltage is applied between electrodes 202 and 204 for a recorded time period until methane production is depressed. The time until methane traces are detected again is noted by controller 210 and a duty cycle of applying voltage across electrodes 202 and 204 for a time interval slightly longer than the time noted for depressing methane production followed by neutral electrode operation for a time period slightly less than the time noted previously for traces of methane to be detected.

This duty cycle is adaptively changed to shorten the time of voltage application and to extend the time between voltage application for purposes of minimizing methane production while maximizing hydrogen production with least application of voltage to electrodes 202 and 204. Voltage level is reduced to provide another variable and adaptively adjusted with respect to the time of voltage application to minimize energy expenditure. This adaptive control algorithm rapidly adjusts for changes in organic waste composition, moisture content, temperature, and other variables.

Figure 12:
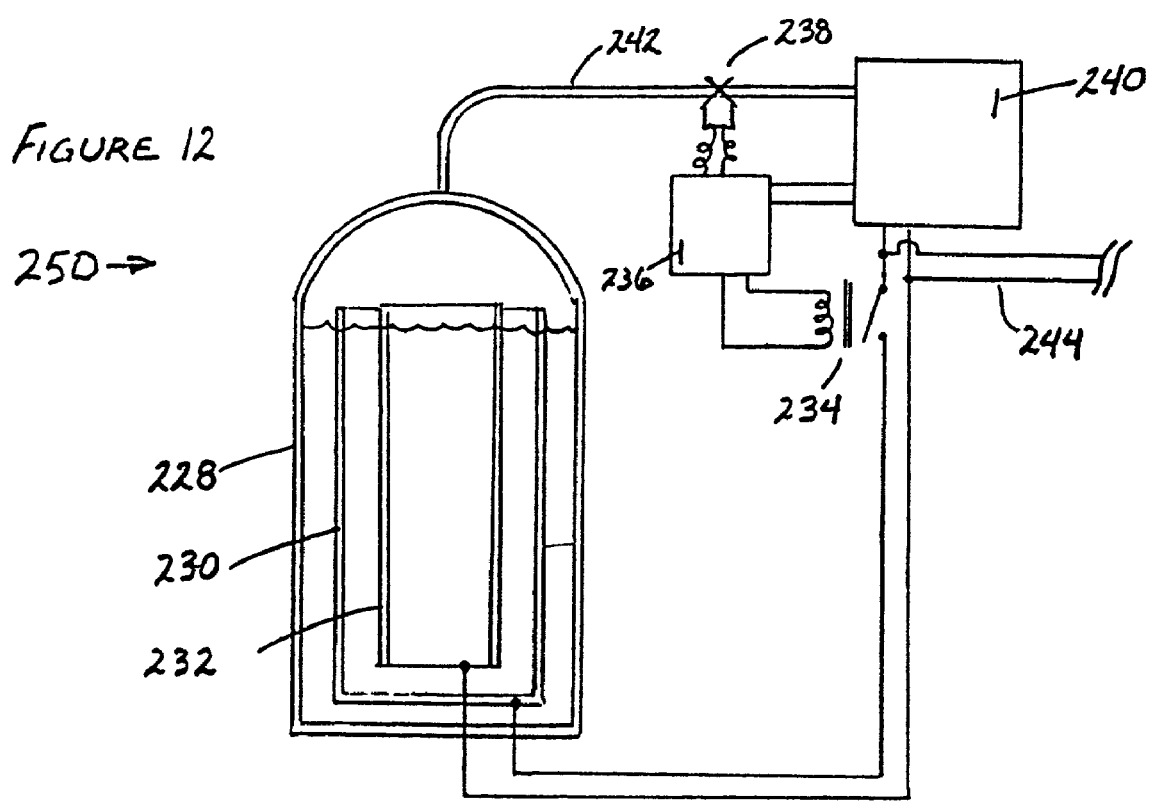
FIG. 12 is a schematically illustrated embodiment showing generation of voltage for practicing the principles of the invention.

FIG. 12 shows an embodiment in which the fuel gas produced by the process of the invention in the presence of electrodes 230 and 232 is in part made available for energy conversion in 240 to electricity by a fuel cell or engine-generator set. Adaptively controlled application of voltage to electrodes 230 and 232 is provided by controller 236 and relay 234 as shown for purposes of minimizing energy consumption per therm of hydrogen produced.

Moreover, adaptive controller 236 provides a control algorithm to minimize methane production while facilitating maximum hydrogen production. Solenoid operated valve 238 controls delivery of fuel gas by line 242 to energy conversion unit 240 as needed to meet adaptively adjusted duty cycle and to meet other demands for electricity as delivered by insulated cables 244. Suitable power for pumping water, providing a heat-pump cycle, or production of electricity at 240 may be by a heat engine and generator, a fuel cell, a thermoelectric generator, or other devices that convert fuel potential energy into electricity.

In many applications, it is preferred to utilize a piston engine and generator in which the engine is fueled with a SmartPlug combination fuel injector and ignition system to facilitate extremely robust operation. SmartPlug operation is disclosed in U.S. Pat. Nos. 5,394,852 and 5,343,699. This enables the raw mixture of hydrogen and carbon dioxide to be used as a very low grade fuel without further conditioning while producing very high thermal efficiency and full rated power in comparison with engine operation on gasoline or diesel fuel. This is a particularly important advantage for remote operation and to bring fuel and power to depressed economies where it is prohibitive to import fossil-based fuels.

Preferential production of hydrogen provides thermodynamic advantages based on faster fuel combustion, wider air/fuel ratio combustion limits, and with SmartPlug operation the engine operates essentially without throttle losses. These thermodynamic advantages provide much higher brake mean effective pressure or "BMEP" for the same heat release in comparisons with gasoline or diesel fuel.

As shown in Table 11, it is possible to actually clean the air with an engine generator running on hydrogen-characterized fuel produced from landfill or sewage organic wastes. The ambient air was cleaned by operation of an engine that is compared in operation between hydrogen and gasoline.

TABLE 11

TEST RESULTS

| AMBIENT AIR TEST: | 29 ppm HC (hydrocarbons) | 0.00 ppm CO (Carbon Monoxide) | 1.0 ppm NO (Nitrogen Monoxide) |
|---|---|---|---|
| ENGINE WITH HYDROGEN OPERATION | | | |
| Idle: | 18 ppm HC | 0.00 ppm CO | 1.0 ppm NO |
| Full Power: | 6 ppm HC | 0.00 ppm CO | 2.0 ppm NO |
| USING GASOLINE AS FUEL IN THE SAME ENGINE: | | | |
| Idle: | 190 ppm HC | 25,000 ppm CO | 390 ppm NO |
| Full Power: | 196 ppm HC | 7,000 ppm CO | 95 ppm NO |

Substantial amounts of carbon dioxide are produced along with hydrogen by operation of electro-conditioned anaerobic digestion of organic wastes. Economical separation of hydrogen from the carbon dioxide is needed for fuel cell applications, for increasing the storage density of hydrogen, and for increasing the value of hydrogen produced. Such separation is provided by the embodiment of FIG. 13. This embodiment also serves the purpose of providing for utilization 25 of the carbon dioxide for various purposes including use in greenhouses or hydroponics and is an important aspect of the invention.

The solubility of carbon dioxide in water is about 21.6 volumes of gas per volume of water at 25 atmospheres pressure and 12° C. (54° F.). Increasing the pressure or decreasing the temperature increases the amount of carbon dioxide dissolved per volume of water. Lowering the pressure or increasing the temperature releases dissolved carbon dioxide. In most areas of the Earth, the ground water is maintained at a temperature that is equal to the mean annual air temperature plus one degree (F) for each 80' of overburden to the saturated zone.

FIG. 13 shows a system for separating carbon dioxide from hydrogen by differential absorption of carbon dioxide within a suitable medium such as water or a hindered amine. In operation, mixed gases consisting of hydrogen, carbon dioxide, and lesser amounts of nitrogen and other gases are forced into the bottom of a column of water 302 approximately 1,000' or higher.

It is generally preferred to use a column of water that is developed by placing a well approximately 1000' below the saturated zone of the local groundwater. This provides the extremely large heat sink benefit of the sub soil including the ground water in the saturated zone where the temperature is generally constant at the desired temperature of 4° C. to 16° C. (40° F. to 60° F.) for most climate zones throughout the year. Water columns that are elevated along mountain slopes are also feasible but may suffer freezing conditions in the winter and unfavorable warming in the summer season.

Mixed gases are delivered to the bottom of tube 304 by a suitable pump (not shown). Mixed gases enter into a suitable scrubber zone such as the helical fin 306 that is attached to tube 304 with a higher elevation at the point of attachment than any other point on the element of rotation that describes the helical surface as shown. Gases thus tend to be buoyed towards tube 304 as they are scrubbed by the absorbing fluid. Carbon dioxide readily enters into solution at the pressure and temperature conditions maintained. Hydrogen exits at the top of the helix into tube 308 and is delivered to the surface for various uses.

Carbon-dioxide rich water is ducted to the surface by coaxial tube 310 as shown. As the head pressure lessens, carbon dioxide bubbles develop and escape upward and create a lower density mixture that is buoyantly lifted to the gas separator section 312 where denser water 25 that has lost the ability to retain carbon dioxide is returned to annular space 302 and sinks the bottom to replace the upward travelling inventory of water that is lifted within tube 310. Carbon dioxide is collected at the top of 310 by tube 314 for various useful purposes.

FIG. 14 shows an embodiment in which energy used to pressurize the hydrogen and carbon dioxide is regeneratively recovered by an expansion engine. Embodiment 400 shows an extremely rugged and simple energy conversion system that combines various renewable resources such as sewage, garbage, and farm wastes with solar energy to supply electricity, hydrogen, and carbon dioxide.

In many situations and applications it is preferred to pressurize water in a suitable vessel 402 to provide for the separation by solubility differences as desired to purify hydrogen. In operation, mixtures of hydrogen and carbon dioxide are forced through tube 404 into pressure vessel 402 at the nominal pressure of 450 PSI. It is preferred to utilize a spiral mixer consisting of a helical fin 406 that causes the mixture of gases to scrub along the surface and form high surface-to-volume ratios. The mixed gases follow an extended path through the water as carbon dioxide is absorbed to allow the hydrogen to be collected at the top of spiral scrubber 406 by tube 408 as shown. Carbon dioxide is absorbed into the water while hydrogen is collected at the top of separator 406 as shown.

Hydrogen is delivered by conduit 408 for immediate use in an engine or fuel cell or it may be stored for future use as needed. Carbon dioxide saturated water is taken from absorber vessel 402 by tube 410 to valve manifold 426 which provides control valves to time the flow of carbon dioxide rich water into each of a group of heat exchangers such as 414, 416, 418, 420, 422, and 424 as shown. Each heat exchanger is provided with an exit a nozzle that is aimed at the blades or buckets of an adjacent fluid motor rotor such as 430, 432, 434, 436, 438, and 440 which deliver work to a common output shaft as shown.

An inventory of water and carbon dioxide solution under pressure is suddenly forced into a preheated heat exchanger such as 414 by briefly opening the control valve that serves 414. As the fluid is heated the temperature and pressure of the fluid increases and it vaporizes and is expelled with very high momentum to power motor 430. Each of the other heat exchanger chambers receives a charge of fluid on a timed basis so that the shaft power from the group of motors shown can be considered to have multiple phase torquing such as six phase if each heat exchanger receives flow at a different times or three phase if two heat exchangers are filled simultaneously. A suitable application of the output of the fluid motor is generator 428 or other useful loads as needed.

It is preferred to provide concentrated radiation to the heat exchangers by a suitable solar collector such as a field of heliostats or a parabolic dish 442 as shown. At times that solar energy is insufficient to meet energy conversion needs, supplemental heat may be applied by combustion from a suitable burner 448. For such supplemental heating it is preferred to use mixtures of carbon dioxide and hydrogen and/or other combustible gases released by anaerobic digestion of organic matter.

After undergoing heating and expansion to a suitably low pressure, carbon dioxide is collected by tube 458 and taken to a suitable application. Water is condensed and collected in reservoir 450 which is cooled by countercurrent heat exchanger 456 by circulation of a suitable heat exchange fluid from 446 to 456 and then through 448 to a suitable cogeneration application. Cooled water is pressurized by pump 454 and returned to pressure vessel 402 to complete the novel carbon dioxide removal and energy conversion cycle.

SUMMARY OF THE INVENTION

Method and apparatus for utilization of intermittently applied voltage for depression of methane production while maximizing hydrogen generation from organic landfill and sewage wastes is provided along with a rational control regime for minimizing the energy expenditure to do so. Renewable biomass and solar resources are combined in a unique energy conversion regime. Production of electricity from an engine operated on hydrogen sourced by the invention is integrated in a synergistic combination that provides regenerative separation of carbon dioxide from fuel gas air and cleaning with carbon sequestration.

The time to dispose of organic materials is preferably reduced by anaerobically digesting such materials in a reaction zone and applying art electric potential across the zone thereby producing hydrogen and carbon dioxide. It is preferred to apply the electric potential occasionally after periods without application of said electric potential.

It is preferred to apply the electric potential at a frequency and for a period to maximize the quantity of hydrogen produced per the amount of electricity consumed. It is preferred to separate carbon dioxide and fuel produced by pressurizing a fluid to a state that provides preferential absorption of carbon dioxide, mixing the fuel and carbon dioxide with the pressurized fluid, and collecting the fuel that remains after preferential absorption of carbon dioxide. Energy conversion efficiency is increased by adding heat to the fluid after preferential absorption of carbon dioxide for the purpose of increasing the amount of work produced by a motor that expands the pressurized fluid, releasing the carbon dioxide in conjunction with the expanding process, and cooling the fluid before the pressurizing step.

The preferred source of such heat is selected from the group including solar energy, heat released by combustion of a portion of the fuel produced, concentrated solar energy, and a combination of solar energy along with heat produced by combustion of a portion of the hydrogen.

An energy conversion process is provided by the steps of anaerobically digesting organic materials to produce carbon dioxide and fuel selected from the group including hydrogen, methane, and mixtures of hydrogen and methane, separating the carbon dioxide from the fuel. The preferred method of separation is comprised of pressurizing a fluid to a state that provides preferential absorption of carbon dioxide, mixing the carbon dioxide and fuel with the fluid, collecting the fuel that remains after said preferential absorption of carbon dioxide, adding heat to the fluid after preferential absorption of carbon dioxide for the purpose of increasing the amount of work produced by a motor that expands pressurized fluid, releasing carbon dioxide in conjunction with the expanding process, and cooling the fluid before the pressurizing step.

In instances that it is preferred to utilize anaerobic digestion to produce hydrogen instead of methane, feedstock organic materials are placed in a reaction zone and an electric potential or voltage is applied across the materials thereby producing hydrogen and carbon dioxide. It is preferred to provide application of intermittent voltage for purposes selected from the group including depression of microorganismal activity that produces methane, enhancement of microorganismal activity that produces hydrogen, and creation of an atmosphere within organic materials that is maintained rich in hydrogen. The process intermittent application of voltage is optimized by feedback information from a gas detector as provided to a controller means. If trace amounts of methane are detected, the voltage is applied for a recorded time period until methane production is depressed, the time until methane traces are detected again is noted by the controller and a duty cycle is provided for applying voltage for a time interval slightly longer than the time noted for depressing methane production followed by neutral electrode operation for a time period slightly less than the time noted previously for traces of methane to be detected In this process, the voltage level is variably reduced to provide an adaptively adjusted control with respect to the time of said voltage application to minimize energy expenditure.

What is claimed is:

1. A process for producing hydrogen from anaerobically digested organic materials comprising:
   (i) applying an intermittent electric potential across said materials to produce hydrogen and carbon dioxide- wherein said electric potential comprises a voltage applied by a voltage source according to a duty cycle that is adjusted by a controller,
   (ii) detecting methane production by gas detection means in communication with said controller;
   (iii) applying a voltage for a first time period until methane production is depressed;
   (iv) discontinuing application of voltage for a second time period;
   (v) detecting resumption of methane production by said gas detection means;
   (vi) applying a voltage for a third time period longer than said first time period;
   (vii) discontinuing application of voltage across electrodes for a fourth time period shorter than the second time period in step (iv);
   (viii) repeating steps (iii)–(vii) iteratively until methane production is minimized and hydrogen production is maximized.

2. A process as in claim 1 in which said intermittent application of said electric potential is timed to occur at a frequency and for a period to maximize the quantity of hydrogen produced per the amount of electricity consumed.

3. A process as in claim 1 wherein a portion of said hydrogen is used by an energy conversion means to supply said electric potential.

4. A process as in claim 1 in which said intermittent application of said electric potential is timed to occur at a frequency and for a period to maximize the quantity of hydrogen produced per the amount of electricity consumed and wherein a portion of said hydrogen is used by an energy conversion means to supply said electric potential.

5. A process as in claim 1 in which said electric potential is applied across electrodes.

6. A process as in claim 1 in which said electric potential is applied across multiple electrodes.

7. The process of claim 6 wherein said electrodes are made from materials selected from the group consisting of lead, copper, steel, brass, carbon, cast iron bars, metal impregnated graphite and electrically conductive graphite.

8. The process of claim 1 wherein said electric potential is adaptively adjusted to minimize electric power consumption while maximizing hydrogen production.

9. The process of claim 1 wherein said electric potential is between 1 and 7 volts.

10. The process of claim 1 wherein said electric potential is between 3 and 6 volts.

11. The process of claim 1 wherein said electric potential is between 3.0 and 4.5 volts.

12. The process of claim 1 wherein said electric potential results in an electric current having low polarization.

13. The process of claim 1 wherein said electric potential results in an electric current having low ohmic losses.

14. The process of claim 1 wherein said voltage is adaptively adjusted to minimize energy expenditure.

* * * * *